(12) United States Patent
Allegretti et al.

(10) Patent No.: US 8,293,788 B2
(45) Date of Patent: Oct. 23, 2012

(54) 2-PHENYLPROPIONIC ACID DERIVATIVES AND PHARMACEUTICAL COMPOSITIONS CONTAINING THEM

(76) Inventors: Marcello Allegretti, L'Aquila (IT); Marla Candida Cesta, L'Aquila (IT); Riccardo Bertini, L'Aquila (IT); Marco Mosca, L'Aquila (IT); Francesco Colotta, L'Aquila (IT)

( * ) Notice: Subject to any disclaimer, the term of this patent is extended or adjusted under 35 U.S.C. 154(b) by 0 days.

(21) Appl. No.: 13/234,125

(22) Filed: Sep. 15, 2011

(65) Prior Publication Data
US 2012/0004264 A1 Jan. 5, 2012

Related U.S. Application Data

(62) Division of application No. 10/592,572, filed as application No. PCT/EP2005/051302 on Mar. 21, 2005, now Pat. No. 8,039,656.

(30) Foreign Application Priority Data

Mar. 23, 2004 (EP) ..................................... 04101202

(51) Int. Cl.
*A61K 31/255* (2006.01)
*A61K 31/165* (2006.01)

(52) U.S. Cl. ............ 514/517; 514/33; 514/428; 514/617
(58) Field of Classification Search .................... 514/33, 514/428, 517, 618
See application file for complete search history.

(56) References Cited

FOREIGN PATENT DOCUMENTS

| WO | WO 00/24710 A1 | 5/2000 |
| WO | WO 01/58852 A2 | 8/2001 |
| WO | WO 02/068377 A1 | 9/2002 |
| WO | WO 03/043625 A1 | 5/2003 |

*Primary Examiner* — Shailendra Kumar
(74) *Attorney, Agent, or Firm* — Birch, Stewart, Kolasch & Birch, LLP

(57) ABSTRACT

4-(trifluoromethanesulfonyloxyphenyl)propionic acid derivatives and pharmaceutical composition containing such compounds are useful in inhibiting the chemotactic activation of neutrophils (PMN leukocytes) induced by the interaction of Interleukin-8 (IL-8) with CXCR1 and CXCR2 membrane receptors. The compounds are used for the prevention and treatment of pathologies deriving from said activation. Notably, these metabolites are devoid of cyclo-oxygenase inhibition activity and are particularly useful in the treatment of neutrophil-dependent pathologies such as psoriasis, ulcerative colitis, melanoma, chronic obstructive pulmonary disease (COPD), bullous pemphigoid, rheumatoid arthritis, idiopathic fibrosis, glomerulonephritis and in the prevention and treatment of damages caused by ischemia and reperfusion.

4 Claims, No Drawings

2-PHENYLPROPIONIC ACID DERIVATIVES AND PHARMACEUTICAL COMPOSITIONS CONTAINING THEM

This application is a Divisional application that claims priority under 35 U.S.C. §120 of application Ser. No. 10/592,572 filed on Jan. 14, 2009, now U.S. Pat. No. 8,039,656, and application Ser. No. 10/592,572 is the national phase under 35 U.S.C. §371 of International Application No. PCT/EP2005/051302 filed on Mar. 21, 2005, which claims priority under 35 U.S.C. §119(a)-(d) of Application No. 04101202.2 filed in the European Patent Office on Mar. 23, 2004.

BRIEF DESCRIPTION OF THE INVENTION

The present invention relates to novel 4-(trifluoromethanesulfonyloxyphenyl)propionic acid derivatives and to pharmaceutical compositions containing them, which are used as inhibitors of the chemotaxis of polymorphonucleate and mononucleate cells, particularly in the treatment of neutrophils-dependent pathologies.

STATE OF THE ART

Particular blood cells (macrophages, granulocytes, neutrophils, polymorphonucleated) respond to a chemical stimulus (when stimulated by substances called chemokines) by migrating along the concentration gradient of the stimulating agent, through a process called chemotaxis. The main known stimulating agents or chemokines are represented by the breakdown products of complement C5a, some N-formyl peptides generated from lysis of the bacterial surface or peptides of synthetic origin, such as formyl-methionyl-leucyl-phenylalanine (f-MLP) and mainly by a variety of cytokines, including Interleukin-8 (IL-8, also referred to as CXCL8). Interleukin-8 is an endogenous chemotactic factor produced by most nucleated cells such as fibroblasts and macrophages.

In some pathological conditions, marked by exacerbated recruitment of neutrophils, a more severe tissue damage at the site is associated with the infiltration of neutrophilic cells. Recently, the role of neutrophilic activation in the determination of damage associated with post ischemia reperfusion and pulmonary hyperoxia was widely demonstrated.

The biological activity of IL-8 is mediated by the interaction of the interleukin with CXCR1 and CXCR2 membrane receptors which belong to the family of seven transmembrane receptors, expressed on the surface of human neutrophils and of certain types of T-cells (L. Xu et al., J. Leukocyte Biol., 57, 335, 1995). Selective ligand are known which can distinguish between CXCR1 and CXCR2: GRO-α is an example of a CXCR2 selective chemotactic factor.

Potential pathogenic role of IL-8 in pulmonary diseases (lung injury, acute respiratory distress syndrome, asthma, chronic lung inflammation, and cystic fibrosis) and, specifically, in the pathogenesis of COPD (chronic obstructive pulmonary disease) through the CXCR2 receptor pathway has been widely described (D. W P Hay and H. M. Sarau., Current Opinion in Pharmacology 2001, 1:242-247).

Characteristic neutrophil accumulation occurs in acute and chronic pathologic conditions, for example in the highly inflamed and therapeutically recalcitrant areas of psoriatic lesions. Neutrophils are chemotactically attracted and activated by the sinergistic action of chemokines, IL-8 and Gro-a released by the stimulated keratinocytes, as well as of the C5a/C5a-desArg fraction produced via the alternative complement pathway activation (T. Terui et al., Exp. Dermatol., 9, 1, 2000).

We have recently described a novel class of "omega-aminoalkylamides of R-2-aryl-propionic acids" as inhibitors of the chemotaxis of polymorphonucleate and mononucleate cells" (WO 02/068377). The novel class include compounds ranging from selective C5a inhibitors to dual C5a/IL-8 inhibitors.

Furthermore, the novel classes of R-2-arylpropionic acid amides and N-acylsulfonamides have been described as effective inhibitors of IL-8 induced neutrophils chemotaxis and degranulation (WO 01/58852; WO 00/24710).

DETAILED DESCRIPTION OF THE INVENTION

We have now found a novel class of 2-(R)-phenylpropionic acid derivatives as inhibitors of the chemotaxis of polymorphonucleate and mononucleate cells. In particular, compounds of the inventions thereof are potent inhibitors of IL-8 induced neutrophils chemotaxis and C5a induced neutrophils and monocytes chemotaxis with improved pharmacokinetic characteristics and pharmacological activity profile.

The present invention thus provides 2-(R)-phenylpropionic acid derivative compounds of formula (I):

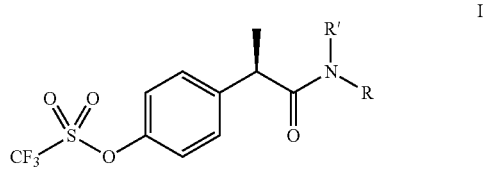

and pharmaceutically acceptable salts thereof,
wherein
R' is selected from
   H, OH and
when R' is H, R is selected from
   H, $C_1$-$C_5$-alkyl, $C_3$-$C_6$-cycloalkyl, $C_2$-$C_5$-alkenyl, $C_1$-$C_5$-alkoxy;
   an heteroaryl group selected from substituted and unsubstituted pyridine, pyrimidine, pyrrole, thiofene, furane, indole, thiazole, oxazole;
   an amino acid residue consisting of straight or branched $C_1$-$C_6$-alkyl, cycloalkyl, $C_2$-$C_6$-alkenyl, $C_1$-$C_6$-phenylalkyl, substituted with one further carboxy (COOH) group;
   a residue of formula —$CH_2$—$CH_2$—Z—($CH_2$—$CH_2$O)nR' wherein R' is H or $C_1$-$C_5$-alkyl, it is an integer from 0 to 2 and Z is oxygen or sulfur;
   a residue of formula —($CH_2$)n—NRaRb wherein n is an integer from 0 to 5 and each Ra and Rb, which may be the same or different, are $C_1$-$C_6$-alkyl, $C_2$-$C_6$-alkenyl or, alternatively, Ra and Rb, together with the nitrogen atom to which they are bound, form a heterocycle from 3 to 7 members of formula (II)

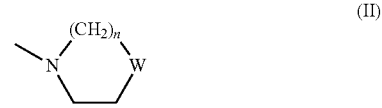

wherein W represents a single bond, O, S, N-Rc, Rc being H, $C_1$-$C_6$-alkyl or $C_1$-$C_6$-alkylphenyl, and n is an integer from 0 to 3;

a residue of formula SO$_2$Rd wherein Rd is C$_1$-C$_6$-alkyl, C$_3$-C$_6$-cycloalkyl, C$_2$-C$_6$-alkenyl, aryl and heteroaryl;

when R' is OH, R is selected from

H, C$_1$-C$_5$-alkyl, C$_3$-C$_6$-cycloalkyl, C$_2$-C$_5$-alkenyl.

The present invention further provides compounds of formula (I) for use as medicaments. In particular, such medicaments are inhibitors of the chemotaxis of polymorphonucleate and mononucleate cells.

Compounds of formula (I) are generically included in the general formulas of the IL-8 and C5a inhibitors previously described in WO 01/58852, WO 00/24710 and WO 02/068377. Compounds of formula (I) have been shown to share significant advantageous characteristics as compared to the particularly preferred compounds of the above cited inventions.

The compounds of the invention belong to the chemical class of aryltriflates. In medicinal chemistry studies triflate group is considered a common bioisosteric replacement of the phenolic hydroxyl or methoxy group; surprisingly, despite the very low potency of the corresponding 4-hydroxyl and 4-methoxy analogues, compounds of formula (I) are potent inhibitors of the IL-8 induced chemotaxis of human PMNs. Additionally, the triflate group on the phenyl ring specifically confers high affinity at the IL-8 receptors CXCR1 and CXCR2. Compounds of formula (I), as compared to the known inhibitors of the IL-8 and/or C5a induced PMN chemotaxis, have surprisingly been found to be very potent inhibitors in the inhibition of GRO-α induced PMN chemotaxis so indicating a specific action on the CXCR2 mediated pathway.

In contrast to the reactive character of aliphatic triflates, aromatic triflates (aryltriflates) are known to be both chemically and biologically stable. Due to the electron withdrawing properties and lipophilicity, the triflate group prevents the oxidation of the aromatic ring via the cytochrome P450 isoenzyme systems. The triflate moiety contributes to enhance the metabolic stability of the compounds of formula (I) slowing down the metabolism (hydroxylation of the aromatic ring/substituent and consequent conjugation) that generally occurs when analogues bearing electron donating groups are administered in vivo.

In association with this property the novel class shows an higher oral bioavailability, an higher t$_{1/2}$, and a lower protein binding in comparison with the classes of the above cited inventions.

These characteristics confer an optimal overall pharmacological profile to these drugs and allow the therapeutic use in different chronic or acute pathological conditions.

When R' is H, preferred R groups are

H, C$_1$-C$_5$ alkyl, C$_3$-C$_6$ cycloalkyl, C$_1$-C$_5$ alkoxy, C$_1$-C$_2$-carboxyalkyl;

a heteroaryl group selected from substituted and unsubstituted pyridine, thiazole, oxazole;

a residue of formula —(CH$_2$)n—NRaRb wherein n is the integer 2 or 3, more preferably 3 and the group NRaRb is N,N-dimethylamine, N,N-diethylamine, 1-piperidyl, 1-pirrolidinyl, 4-morpholyl, 1-piperazinyl, 1-(4-methyl)piperazinyl;

a residue of formula SO$_2$Rd wherein Rd is C$_1$-C$_2$-alkyl, C$_3$-C$_6$ cycloalkyl.

When R' is OH, preferred R groups are

H, C$_1$-C$_5$ alkyl, C$_3$-C$_6$ cycloalkyl.

Particularly preferred compounds of the invention are:

1—R(−)-2-[(4'-trifluoromethanesulfonyloxy)phenyl]-N-methanesulfonyl propionamide;

1a—R(−)-2-[(4'-trifluoromethanesulfonyloxy)phenyl]-N-methanesulfonyl propionamide sodium salt;

2—R(−)-2-[(4'-trifluoromethanesulfonyloxy)phenyl]propionamide;

3—R(−)-2-[(4'-trifluoromethanesulfonyloxy)phenyl]-N-methyl propionamide;

4—R(−)-2-[(4'-trifluoromethanesulfonyloxy)phenyl]-N-isopropoxy propionamide;

5—R(−)-2-[(4'-trifluoromethanesulfonyloxy)phenyl]-N-cyclopentyl propionamide;

6—R(−)-2-[(4'-trifluoromethanesulfonyloxy)phenyl]-N-[3-(N-piperidinyl)propyl]propionamide;

6a—R(−)-2-[(4'-trifluoromethanesulfonyloxy)phenyl]-N-[3-(N-piperidinyl)propyl]propionamide hydrochloride;

7—R(−)-2-[(4'-trifluoromethanesulfonyloxy)phenyl]-N-[2-(N'-pirrolidinyl)ethyl]propionamide;

7a—R(−)-2-[(4'-trifluoromethanesulfonyloxy)phenyl]-N-[2-(N-pirrolidinyl)ethyl]propionamide hydrochloride;

8—R(−)-2-[(4'-trifluoromethanesulfonyloxy)phenyl]-N-[3-(N-pirrolidinyl)propyl]propionamide;

8a—R(−)-2-[(4'-trifluoromethanesulfonyloxy)phenyl]-N-[3-(N'-pirrolidinyl)propyl]propionamide hydrochloride;

9—R(+)-2-[(4'-trifluoromethanesulfonyloxy)phenyl]-N-(2-hydroxyethoxyethyl) propionamide;

10—R(−)-2-[(4'-trifluoromethanesulfonyloxy)phenyl]-N-[2-(4'-trifluoromethyl)thiazolyl]propionamide;

11—R(−)-2-[(4'-trifluoromethanesulfonyloxy)phenyl]-N-methyl-N-hydroxy propionamide. Most preferred compound in the list is compound 1 and the related sodium salt 1a.

The compounds of the invention are potent inhibitors of the human PMNs chemotaxis induced by IL-8. The compounds of the invention wherein R is a residue of formula —(CH$_2$)n—NRaRb are dual inhibitors of the C5a induced and IL-8 induced PMNs chemotaxis.

The compounds of the invention of formula (I) are generally isolated in the form of their addition salts with both organic and inorganic pharmaceutically acceptable acids or bases. Examples of such acids are selected from hydrochloric acid, sulfuric acid, phosphoric acid, metansulfonic acid, fumaric acid, citric acid.

Examples of such bases are sodium hydroxide, potassium hydroxide, calcium hydroxide, (D,L)-Lysine, L-Lysine, tromethamine.

Compounds of formula (I) are obtained starting from R(−)-2-(4'-trifluoromethanesulfonyloxyphenyl)propionic acid according to the methodologies previously described in WO 01/58852, WO 00/24710 and WO 02/068377.

For example compounds of formula (I), wherein R is SO$_2$Rd and Rd is C$_1$-C$_2$-alkyl or C$_3$-C$_6$ cycloalkyl, can be obtained by treatment of an equimolecular amount of R(−)-2-(4'-trifluoromethanesulfonyloxyphenyl)propionic acid with an equimolecular amount of a suitable sulfonamide RdSO$_2$NH$_2$, in a inert solvent, in the presence of an equimolecular amount or of a slight excess of a condensing agent, for example a carbodiimide (such as dicyclohexylcarbodiimide), a soluble carbodiimide (such as N-(3-dimethyl-amino-propyl)-N'-ethylcarbodiimide hydrochloride) or 1,1'-carbonyldiimidazole and of a counterbase selected from the group consisting of triethylamine, 4-(N,N-dimethylamino)-pyridine, 1,8-diazabicyclo[5.4.0]undec-7-ene, and 1,5-diazabicyclo[4.3.0]non-5-ene.

The compounds of the invention of formula (I) were evaluated in vitro for their ability to inhibit chemotaxis of polymorphonucleate leukocytes (hereinafter referred to as PMNs) and monocytes induced by the fractions of IL-8 and GRO-α and C5a. For this purpose, in order to isolate the PMNs from heparinized human blood, taken from healthy adult volunteers, mononucleates were removed by means of sedimentation on dextran (according to the procedure disclosed by W. I. Ming et al., J. Immunol., 138, 1469, 1987) and red blood cells by a hypotonic solution. The cell vitality was calculated by exclusion with Trypan blue, whilst the ratio of the circulating polymorphonucleates was estimated on the cytocentrifugate after staining with Diff Quick.

In the IL-8 induced chemotaxis assay human recombinant IL-8 (Pepro Tech) was used as stimulating agents in the chemotaxis experiments: the lyophilized protein was dissolved in a volume of HBSS containing 0.2% bovin serum albumin (BSA) so thus to obtain a stock solution having a concentration of $10^{-5}$ M to be diluted in HBSS to a concentration of $10^{-9}$ M, for the chemotaxis assays.

GRO-α induced chemotaxis inhibition was evaluated in an analogous assay.

In the C5a induced chemotaxis essay the fractions hrC5a and hrC5a-desArg (Sigma) were used as stimulating agents in chemotaxis experiments, obtaining practically identical results, Lyophilized C5a was dissolved in a volume of HBSS containing 0.2% BSA so as to obtain a stock solution having a concentration of $10^{-5}$ M, to be diluted in HBSS to a concentration of $10^{-9}$ M, for the chemotaxis assays.

In the chemotaxis experiments, the PMNs were incubated with the compounds of the invention of formula (I) for 15' at 37° C. in an atmosphere containing 5% $CO_2$.

The chemotactic activity of the C5a was evaluated on human circulating polymorphonucleates (PMNs) resuspended in HBSS at a concentration of $1.5 \times 10^6$ PMNs per ml.

During the chemotaxis assay (according to W. Falket et al., J. Immunol. Methods, 33, 239, 1980) PVP-free filters with a porosity of 5 μm and microchambers suitable for replication were used.

The compounds of the invention in formula (I) were evaluated at a concentration ranging between $10^{-6}$ and $10^{-10}$ M; for this purpose they were added, at the same concentration, both to the lower pores and the upper pores of the microchamber. Evaluation of the ability of the compounds of the invention of formula (I) to inhibit the chemotaxis of human monocytes was carried out according to the method disclosed by Van Damme J. et al. (Eur. J. Immunol., 19, 2367, 1989).

Protein Binding was determined as follows: Duplicate rat plasma samples of each compound at 50 μg/mL concentration were incubated at 37° C. for 20 minutes under gentle shaking. Then samples were ultrafiltrated through Centrifree® micropartition devices by centrifugation at 1500 g for 15 minutes. The ultrafiltrate was subjected to HPLC-MS/MS quantitative analysis (Column Luna C18, 150×2 mm ID 5 μm (Phenomenex), mobile phase: eluent A) 0.02M $HCOO^-NH_4^+$ (pH 4.3 with HCOOH); eluent B) $CH_3OH$).

The pharmacokinetic profile ($t_{1/2}$, oral bioavailability, etc) of claimed compounds was evaluated in male mice after intravenous and oral administration. The pharmacokinetic analysis was performed using compounds plasmatic concentrations at different times. The data were evaluated by Kinetica 2000™, Version 3.0 Software [InnaPhase Corporation, World headquarters, 1700 Race Street, Philadelphia, Pa. 19103 USA].

The compounds of formula (I), evaluated ex vivo in the blood in toto according to the procedure disclosed by Patrignani et al., in J. Pharmacol. Exper. Ther., 271, 1705, 1994, were found to be totally ineffective as inhibitors of cyclooxygenase (COX) enzymes.

In most cases, the compounds of formula (I) do not interfere with the production of $PGE_2$ induced in murine macrophages by lipopolysaccharides stimulation (LPS, 1 μg/mL) at a concentration ranging between $10^{-5}$ and $10^{-7}$ M. Inhibition of the production of $PGE_2$ which may be recorded, is mostly at the limit of statistical significance, and more often is below 15-20% of the basal value. The reduced effectiveness in the inhibition of the CO constitutes an advantage for the therapeutical application of compounds of the invention in as much as the inhibition of prostaglandin synthesis constitutes a stimulus for the macrophage cells to amplify synthesis of TNF-α (induced by LPS or hydrogen peroxide) that is an important mediator of the neutrophilic activation and stimulus for the production of the cytokine Interleukin-8.

Inhibitors of CXCR1 and CXCR2 activation find useful applications, as above detailed, particularly in treatment of chronic inflammatory pathologies (e.g. psoriasis) in which the activation of both IL-8 receptors is supposed to play a crucial pathophysiological role in the development of the disease.

In fact, activation of CXCR1 is known to be essential in IL-8-mediated PMN chemotaxis (Hammond M et al, J Immunol, 155, 1428, 1995). On the other hand, activation of CXCR2 activation is supposed to be essential in IL-8-mediated epidermal cell proliferation and angiogenesis of psoriatic patients (Kulke R et al., J Invest Dermatol, 110, 90, 1998).

In addition, CXCR2 antagonists find particularly useful therapeutic applications in the management of important pulmonary diseases like chronic obstructive pulmonary disease COPD (D. WP Hay and H. M. Sarau., Current Opinion in Pharmacology 2001, 1:242-247).

In view of the experimental evidence discussed above and of the role performed by Interleukin-8 (IL-8) and congenetics thereof in the processes that involve the activation and the infiltration of neutrophils, the compounds of the invention are particularly useful in the treatment of diseases such as psoriasis (R. J. Nicholoff et al., Am. J. Pathol., 138, 129, 1991), intestinal chronic inflammatory pathologies such as ulcerative colitis (Y. R. Mahida et al., Clin. Sci., 82, 273, 1992), chronic obstructive pulmonary disease (COPD), bullous pemphigo, rheumatoid arthritis (M. Selz et al., J. Clin. Invest., 87, 463, 1981), idiopathic fibrosis (E. J. Miller, previously cited, and P. C. Cane et al., J. Clin. Invest., 88, 1882, 1991), glomerulonephritis (T. Wada et al., J. Exp. Med., 180, 1135, 1994).

The compounds of the present invention are also effective in the prevention and treatment of damages caused by ischemia and reperfusion, in particular in the protection from functional injury in organ transplantation, particularly kidney transplantation.

In an experimental model of kidney transplantation in rats, the compounds of the invention have proved active in the preservation of renal function immediately after ischemia/reperfusion injury which follows syngeneic kidney transplantation, in that they prevent leukocyte infiltration in the transplant which occurs following post-ischemic reperfusion.

Experimental Model of Kidney Transplantation in Rats.

The study was performed in a syngeneic kidney transplant model using rats as donor and graft recipients. An anastomosis was created between the recipient and the donor renal artery as well as renal vein with end-to-end anastomosis. Vascular clamps were released after 30 minutes (warm ischemia). The native right kidney was then removed. Animals were placed in individual metabolic cages for measurements of daily urine output as an index of renal function recovery. After 16 and 24 hours, renal function was assessed by measuring plasma creatinine concentration. Twenty-four hours after kidney transplantation, the animals were sacrificed. The kidney graft was removed, cut in slices and put in Dubosq-Brazil solution for the analysis of conventional histology by light microscopy. Moreover, additional kidney fragments were frozen in liquid nitrogen and used for immunohistochemical analysis of inflammatory cell infiltrate (polymorphonuclear cells, MHC class II positive cells).

All compounds of the invention showed protection of injury in transplanted rats treated i.v. before kidney transplantation and s.c. two hours after transplantation, at a concentration ranging from 5 mg/Kg to 30 mg/Kg.

Furthermore, the compounds of the invention are particularly useful in the treatment of melanoma and angiogenesis.

The in vitro activity on melanoma cells has been determined as follows:

Melanoma Cell Proliferation

Ninety-six-well plates containing 2-6×10³ melanoma cells/well were pretreated with selected compounds of the invention, stimulated with interleukin-8 (CXCL8) and cultured for 3-4 days. 3-(4,5-dimethylthiazolyl-2)-2,5-diphenyltetrazolium bromide (MTT, 400 μg/ml) was then added to each well and incubated for 2 hours. The medium was removed and 100 μl of dimethyl sulfoxide was added to lyse cells. Absorbance value, determined on a microplate reader, measured changes in cell proliferation.

Invasion Assay Through Matrigel

Melanoma cells were plated (5×10³ cells on six-well plates) and allowed to attach for 24 hours. After 5 days of treatment with selected compounds of the invention, cells were released from the plates by a brief exposure to trypsin-ethylenediaminetetraacetic acid, counted, and centrifuged. Biocoat Matrigel invasion chambers were primed according to the manufacturer's directions. CXCL8 dissolved in serum free medium was placed in the lower well to act as a chemoattractant, and 3×10³ cells in 500 μl of serum free medium were placed in the upper chamber of the Matrigel plate and incubated at 37° C. for 22 hours. Cells on the lower surface of the filter were stained with Diff-Quick and quantified with an image analyzer attached to microscope.

It is therefore a further object of the present invention to provide the use of compounds of formula (I) in the manufacture of a medicament for the treatment of psoriasis, ulcerative colitis, melanoma, angiogenesis, chronic obstructive pulmonary disease (COPD), bullous pemphigo, rheumatoid arthritis, idiopathic fibrosis, glomerulonephritis and in the prevention and treatment of damages caused by ischemia and reperfusion.

Table I reports the biological activity of exemplary compounds of the present invention in comparison with exemplary compounds of the above cited patent documents.

TABLE I

| N. | | PMN migration by IL-8 % of inhibition ($10^{-9}$M) | PMN migration by GROα % of inhibition ($10^{-8}$M) | PMN migration by C5a % of inhibition ($10^{-8}$M) |
|---|---|---|---|---|
| | IL-8 inhibitors | | | |
| | 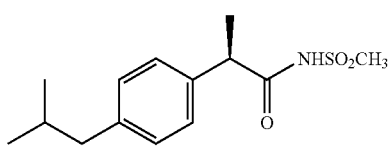<br>WO 00/24710 | 50 ± 12 | 10 ± 18 | Inactive[#] |
| | 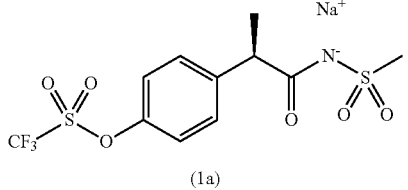<br>(1a) | 58 ± 9 | 61 ± 6 | Inactive[#] |
| | 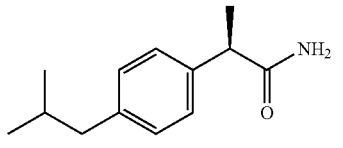<br>WO 01/58852 | 57 ± 12 | 10 ± 7 | Inactive[#] |
| | 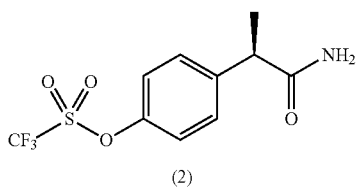<br>(2) | 64 ± 2 | 61 ± 3 | Inactive[#] |

TABLE I-continued

| N. | | PMN migration by IL-8 % of inhibition ($10^{-9}$M) | PMN migration by GROα % of inhibition ($10^{-8}$M) | PMN migration by C5a % of inhibition ($10^{-8}$M) |
|---|---|---|---|---|
| | Dual IL-8/C5a inhibitors | | | |
| 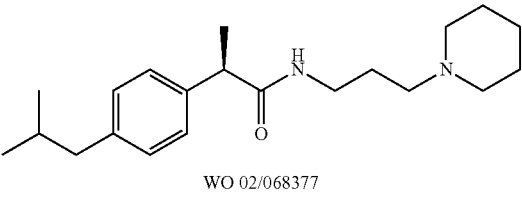 WO 02/068377 | | 44 ± 5 | 39 ± 10 | 55 ± 6 |
| 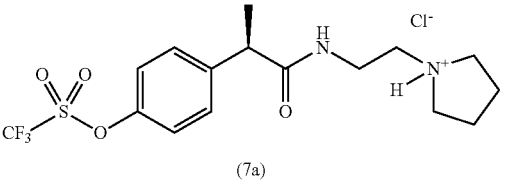 (7a) | | 52 ± 12 | Inactive[#] | 65 ± 18 |
| 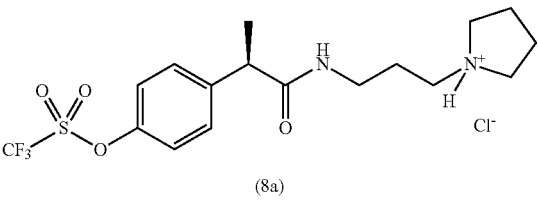 (8a) | | 51 ± 13 | Inactive[#] | 67 ± 10 |

[#]Tested at $10^{-6}$M

Table II reports data of chemical-physical, pharmacological and pharmacokinetic characteristics of exemplary compounds of formula (I) in comparison with exemplary compounds of the above cited patent documents. Compounds of formula (I) show an higher oral bioavailability, an higher $t_{1/2}$, and a lower protein binding in comparison with the exemplary compounds.

TABLE II

| N. | Protein Binding (50 μg/mL) | $t_{1/2}$ (h) | Oral Bioavailability |
|---|---|---|---|
| IL-8 inhibitors | | | |
| 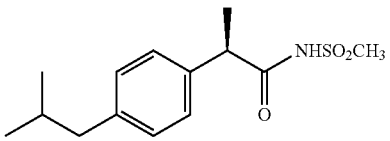 WO 00/24710 | 99.98% | 0.4 | 80% |
| 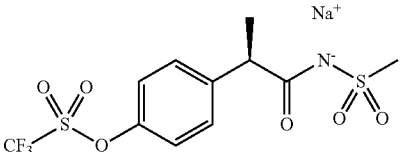 (1a) | 99.00% | 24.7 | ~100% |

TABLE II-continued

| N. | Protein Binding (50 µg/mL) | $t_{1/2}$ (h) | Oral Bioavailability |
|---|---|---|---|
| WO 01/58852 | 98.40% | 0.4 | 35% |
| (2) | 93.80% | 2.3 | 95% |
| Dual IL-8/C5a inhibitors | | | |
| WO 02/068377 | 85.00% | 1.7 | 30% |
| (7a) | 70.36% | 3.4 | 80% |
| (8a) | 64.07% | 2.4 | 90% |

Pharmaceutical compositions comprising a compound of the invention and a suitable carrier thereof, are also within the scope of the present invention.

The compounds of the invention, together with a conventionally employed adjuvant, carrier, diluent or excipient may, in fact, be placed into the form of pharmaceutical compositions and unit dosages thereof, and in such form may be employed as solids, such as tablets or filled capsules, or liquids such as solutions, suspensions, emulsions, elixirs, or capsules filled with the same, all for oral use, or in the faun of sterile injectable solutions for parenteral (including subcutaneous) use. Such pharmaceutical compositions and unit dosage forms thereof may comprise ingredients in conventional proportions, with or without additional active compounds or principles, and such unit dosage forms may contain any suitable effective amount of the active ingredient commensurate with the intended daily dosage range to be employed.

When employed as pharmaceuticals, the compounds of this invention are typically administered in the form of a pharmaceutical composition. Such compositions can be prepared in a manner well known in the pharmaceutical art and comprise at least one active compound. Generally, the compounds of this invention are administered in a pharmaceutically effective amount. The amount of the compound actually administered will typically be determined on the basis of relevant circumstances including the condition to be treated, the chosen route of administration, the actual compound administered, the age, weight, and response of the individual patient, the severity of the patient's symptoms, and the like.

The pharmaceutical compositions of the invention can be administered by a variety of routes including oral, rectal, transdermaldermal, subcutaneous, intravenous, intramuscular, and intranasal. Depending on the intended route of delivery, the compounds are preferably formulated as either injectable or oral compositions. The compositions for oral administration can take the form of bulk liquid solutions or suspensions, or bulk powders. More commonly, however, the compositions are presented in unit dosage forms to facilitate accurate dosing. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient. Typical unit dosage forms include prefilled, premeasured ampoules or syringes of the liquid compositions or pills, tablets, capsules or the like in the case of solid compositions. In such compositions, the acid compound is usually a minor component (from about 0.1 to about 50% by weight or preferably from about 1 to about 40% by weight) with the remainder being various vehicles or carriers and processing aids helpful for forming the desired dosing form.

Liquid forms suitable for oral administration may include a suitable aqueous or nonaqueous vehicle with buffers, suspending and dispensing agents, colorants, flavors and the like. Liquid forms, including the injectable compositions described herebelow, are always stored in the absence of light, so as to avoid any catalytic effect of light, such as hydroperoxide or peroxide formation. Solid forms may include, for example, any of the following ingredients, or compounds of a similar nature: a binder such as microcrystalline cellulose, gum tragacanth or gelatine; an excipient such as starch or lactose, a disintegrating agent such as alginic acid, Primogel, or corn starch; a lubricant such as magnesium stearate; a glidant such as colloidal silicon dioxide; a sweetening agent such as sucrose or saccharin; or a flavoring agent such as peppermint, methyl salicylate, or orange flavoring.

Injectable compositions are typically based upon injectable sterile saline or phosphate-buffered saline or other injectable carriers known in the art. As above mentioned, the acid derivative of formula (I) in such compositions is typically a minor component, frequently ranging between 0.05 to 10% by weight with the remainder being the injectable carrier and the like. The mean daily dosage will depend upon various factors, such as the seriousness of the disease and the conditions of the patient (age, sex and weight). The dose will generally vary from 1 mg or a few mg up to 1500 mg of the compounds of formula (I) per day, optionally divided into multiple administrations. Higher dosages may be administered also thanks to the low toxicity of the compounds of the invention over long periods of time.

The above described components for orally administered or injectable compositions are merely representative. Further materials as well as processing techniques and the like are set out in Part 8 of "Remington's Pharmaceutical Sciences Handbook", 18th Edition, 1990, Mack Publishing Company, Easton, Pa., which is incorporated herein by reference.

The compounds of the invention can also be administered in sustained release forms or from sustained release drug delivery systems. A description of representative sustained release materials can also be found in the incorporated materials in the Remington's Handbook as above.

The present invention shall be illustrated by means of the following examples which are not construed to be viewed as limiting the scope of the invention.

EXAMPLES

Example of abbreviations are: THF for tetrahydrofuran, DBU for 1,8-Diazabicyclo[5.4.0]undec-7-ene.

All the compounds described in the examples are obtained starting from R(-)-2-(4'-trifluoromethanesulfonyloxyphenyl)propionic acid prepared as previously described in WO 03/043625

Example 1

R(-)-2-[(4'-trifluoromethanesulfonyloxy)phenyl]-N-methanesulfonyl propionamide 1,1'-Carbonyldiimidazole (7.21 g, 44.5 mmol) is added at room temperature to a solution of R(-)-2-(4'-trifluoromethanesulfonyloxyphenyl)propionic acid (13.28 g, 44.5 mmol) in anhydrous $CH_2Cl_2$ (130 mL). The resulting solution is left under stirring for 1 h30'. Then methanesulfonamide (4.23 g, 44.5 mmol) is added and, after 1 h at room temperature, DBU (6.65 mL, 44.5 mmol). The resulting mixture is left stirring at room temperature overnight. The organic phase is washed with 0.5M HCl (2×50 mL), 5% $NaH_2PO_4$ solution (3×50 mL), and water to neutrality. After drying on $Na_2SO_4$ and evaporation of the solvent, the obtained residue is treated with isopropyl ether. The formed precipitate is filtered off and mother liquors are evaporated under reduced pressure to give a crude solid which, after pulping in n-hexane (50 mL) at room temperature for 2 h, affords the pure R(-)-2-[(4'-trifluoromethanesulfonyloxy)phenyl]-N-methanesulfonyl propionamide (13.2 g, 35.15 mmol) as white powder (yield 79%).

m.p. 98°-100° C. $[\alpha]_D$=-49.4 (c=0.5; $CH_3OH$). $^1$H-NMR ($CDCl_3$): δ 7.40 (d, 2H, J=7 Hz); 7.23 (d, 2H, J=7 Hz); 3.68 (q, 1H, J=7 Hz); 3.15 (s, 3H); 1.42 (d, 3H, J=7 Hz).

Example 1a

R(-)-2-[(4'-trifluoromethanesulfonyloxy)phenyl]-N-methanesulfonyl propionamide sodium salt R(-)-2-[(4'-trifluoromethanesulfonyloxy)phenyl]-N-methanesulfonyl propionamide (6.89 g, 18.35 mmol) is dissolved in ethanol (35 mL) and 1M NaOH (volumetric standard) (18.35 mL) is added dropwise. The solution is left stirring for 30' at room temperature. The alcohol is evaporated under reduced pressure and the aqueous solution is frozen and lyophilised overnight. The pure sodium salt is obtained as white powder (7.29 g, 18.35 mmol).

$[\alpha]_D$=-27.2 (c=0.5; $CH_3OH$)

Example 2

R(-)-2-[(4'-trifluoromethanesulfonyloxy)phenyl] propionamide

Thionyl chloride (4.8 mL, 67 mmol) is added at room temperature to a solution of R(-)-2-(4'-trifluoromethanesulfonyloxyphenyl)propionic acid (10 g, 33.5 mmol) in anhydrous toluene (10 mL). The solution is refluxed under stirring for 2 h. After cooling at room temperature, toluene is evaporated under reduced pressure and the crude oily residue is dissolved in $CH_2Cl_2$ (25 mL) and ammonia is bubbled into the solution for 1 h. The organic solution is washed with water (3×15 mL), dried on $Na_2SO_4$ and evaporated under reduced pressure to give a slightly brown crude solid purified by pulping in n-hexane (100 mL) for 2 hours. The pure R(-)-2-[(4'-trifluoromethanesulfonyloxy)phenyl]propionamide (8.1 g, 27.2 mmol) is isolated by filtration under vacuum as white powder (yield 81%).

m.p. 67°-69° C. $[\alpha]_D$=-12 (c=1; $CH_3OH$). $^1$H-NMR ($CDCl_3$): δ 7.69 (d, 2H, J=7 Hz); 7.22 (d, 2H, J=7 Hz); 5.37 (bs, 2H, $CONH_2$); 3.63 (q, 1H, J=7 Hz); 1.53 (d, 3H, J=7 Hz).

Example 3

R(−)-2-[(4'-trifluoromethanesulfonyloxy)phenyl]-N-methyl propionamide

Thionyl chloride (4 mL) is added at room temperature to a solution of R(−)-2-(4'-trifluoromethanesulfonyloxyphenyl) propionic acid (1 g, 3.35 mmol) in anhydrous toluene (2.5 mL). The solution is refluxed under stirring for 2 h. After cooling at room temperature, toluene is evaporated under reduced pressure and the crude oily residue is dissolved in $CH_2Cl_2$ (10 mL). The organic solution is added dropwise to a solution of methylamine (0.414 mL, 10.08 mmol) in $CH_2Cl_2$ (5 mL). The mixture is left stirring at room temperature for 3 h. The solvent is evaporated under reduced pressure to distill off the excess amine and the crude is diluted again with $CH_2Cl_2$ (10 mL), washed with a saturated solution of $NaHCO_3$ (2×5 mL) and with water (3×15 mL), dried on $Na_2SO_4$ and evaporated under reduced pressure to give a crude residue as orange oil. The crude is purified by flash chromatography (eluent: $CH_2Cl_2/CH_3OH$ 98:2) to obtain pure R(−)-2-[(4'-trifluoromethanesulfonyloxy)phenyl]-N-methyl propionamide as transparent oil (0.78 g, 2.51 mmol) (yield 75%).

$[\alpha]_D$=−19 (c=0.5; $CH_3OH$). $^1$H-NMR ($CDCl_3$): δ 7.48 (d, 2H, J=7 Hz); 7.24 (d, 2H, J=7 Hz); 5.35 (bs, 1H, CONH); 3.55 (q, 1H, J=7 Hz); 2.72 (d, 3H, J=3 Hz); 1.55 (d, 3H, J=7 Hz).

Example 4

R(−)-2-[(4'-trifluoromethanesulfonyloxy)phenyl]-N-isopropoxy propionamide

To a suspension of N-isopropylhydroxylamine hydrochloride (0.14 g, 1.67 mmol) and $NaHCO_3$ (0.19 g, 3.34 mmol) in anhydrous THF (5 mL), R(−)-2-(4'-trifluoromethanesulfonyloxyphenyl)propionyl chloride, prepared starting from the corresponding acid (0.5 g, 1.67 mmol) as described in the example 3, is added and the solution left stirring at room temperature for 3 h. After solvent evaporation the crude is diluted with $CH_2Cl_2$ (10 mL), washed with water (2×10 mL), dried on $Na_2SO_4$ and evaporated under reduced pressure to give an oily residue. The crude is purified by treatment with n-hexane and the formed precipitate, after filtration, affords the pure R(−)-2-[(4'-trifluoromethanesulfonyloxy)phenyl]-N-isopropoxy propionamide as white powder (0.45 g, 1.28 mmol) (yield 77%).

$[\alpha]_D$=−24 (c=0.5; $CH_3OH$). $^1$H-NMR ($CDCl_3$): δ 8.15 (bs, 1H, CONH); 7.45 (d, 2H, J=7 Hz); 7.20 (d, 2H, J=7 Hz); 3.65 (m, 1H); 3.50 (q, 1H, J=7 Hz); 1.55 (d, 3H, J=7 Hz); 1.2 (d, 6H, J=3 Hz).

According the same procedure described for Example 3, the following amides have been synthesised starting from commercial amines or from amines prepared according the procedure described in WO 01/58852; WO 00/24710 and WO 02/068377:

Example 5

R(−)-2-[(4'-trifluoromethanesulfonyloxy)phenyl]-N-cyclopentyl propionamide $[\alpha]_D$=−35 (c=1; $CH_3OH$). $^1$H-NMR ($CDCl_3$): δ 7.52 (d, 2H, J=7 Hz); 7.28 (d, 2H, J=7 Hz); 5.55 (bs, 1H, CONH); 3.58 (q, 1H, J=7 Hz); 3.48 (m, 1H); 2.85 (m, 4H); 2.36 (m, 4H); 1.58 (d, 3H, J=7 Hz),

Example 6

R(−)-2-[(4'-trifluoromethanesulfonyloxy)phenyl]-N-[3-(N'-piperidinyl)propyl]propionamide $[\alpha]_D$=−26 (c=2; $CH_3OH$). $^1$H-NMR ($CDCl_3$): δ 8.11 (bs, 1H, CONH); 7.72 (d, 2H, J=7 Hz); 7.25 (d, 2H, J=7 Hz); 3.88 (q, 1H, J=7 Hz); 3.55 (m, 2H); 3.30-2.95 (m, 3H); 2.70 (m, 2H); 2.48 (m, 2H); 2.25 (m, 2H); 2.05 (m, 2H); 2.00-1.74 (m, 2H); 1.54 (d, 3H, J=7 Hz).

Example 6a

R(−)-2-[(4'-trifluoromethanesulfonyloxy)phenyl]-N-[3-(N'-piperidinyl)propyl]propionamide hydrochloride R(−)-2-[(4'-trifluoromethanesulfonyloxy)phenyl]-N-[3-(N'-piperidinyl)propyl]propionamide (0.15 g, 0.35 mmol) is dissolved in $CH_2Cl_2$ (3 mL). 3N HCl (0.5 mL) is added and, after stirring at room temperature for 1 h, solvents are evaporated under reduced pressure and the crude is diluted with anhydrous ethyl ether (5 mL). The formed precipitate is isolated by filtration under vacuum to give pure R(−)-2-[(4'-trifluoromethanesulfonyloxy)phenyl]-N-[3-(N-piperidinyl) propyl]propionamide hydrochloride as white powder (0.128 g, 0.28 mmol).

$[\alpha]_D$=−12 (c=2; $CH_3OH$).

Example 7

R(−)-2-[(4'-trifluoromethanesulfonyloxy)phenyl]-N-[2-(N'-pirrolidinyl)ethyl]propionamide $[\alpha]_D$=−34 (c=1; $CH_3OH$). $^1$H-NMR ($CDCl_3$): δ 8.65 (bs, 1H, CONH); 7.75 (d, 2H, J=7 Hz); 7.22 (d, 2H, J=7 Hz); 4.02 (m, 2H); 3.85-3.74 (m, 3H); 3.31 (m, 2H); 3.0-2.80 (m, 2H); 2.41-2.12 (m, 4H); 1.65 (d, 3H, J=7 Hz).

Example 7a

R(−)-2-[(4'-trifluoromethanesulfonyloxy)phenyl]-N-[2-(N-pirrolidinyl)ethyl]propionamide hydrochloride The compound has been prepared following the procedure described in Example 6a.

$[\alpha]_D$=−22 (c=1; $CH_3OH$).

Example 8

R(−)-2-[(4'-trifluoromethanesulfonyloxy)phenyl]-N-[3-(N-pirrolidinyl)propyl]propionamide $[\alpha]_D$=−41 (c=1; $CH_3OH$). $^1$H-NMR ($CDCl_3$): δ 8.01 (bs, 1H, CONH); 7.62 (d, 2H, J=7 Hz); 7.15 (d, 2H, J=7 Hz); 3.80 (q, 1H, J=7 Hz); 3.52 (m, 2H); 3.31 (m, 2H); 2.95 (m, 2H); 2.78 (m, 2H); 2.15-1.90 (m, 6H); 1.55 (d, 3H, J=7 Hz).

Example 8a

R(−)-2-[(4'-trifluoromethanesulfonyloxy)phenyl]-N-[3-(N'-pirrolidinyl)propyl]propionamide hydrochloride The compound has been prepared following the procedure described in Example 6a.

$[\alpha]_D$=−17 (c=1; $CH_3OH$).

Example 9

R(+)-2-[(4'-trifluoromethanesulfonyloxy)phenyl]-N-(2-hydroxyethoxyethyl) propionamide A solution of R(-)-2-(4'-trifluoromethanesulfonyloxyphenyl)propionic acid (0.53 g, 1.79 mmol) in thionyl chloride (1 mL) is refluxed under stirring for 2 h. After cooling at room temperature and evaporation under reduced pressure, the crude oily residue is dissolved in $CH_2Cl_2$ (2 mL) and added dropwise to a solution of 2-hydroxyethoxyethylamine (0.36 mL, 3.58 mmol) in $CH_2Cl_2$ (4 mL). The mixture is left stirring at room temperature overnight. The solution is washed with water (3×10 mL), dried on $Na_2SO_4$ and evaporated under reduced pressure to give a crude oily residue. The crude is purified by treatment in isopropyl ether (overnight at room temperature) to give, after filtration, R(+)-2-[(4'-trifluoromethanesulfonyloxy)phenyl]-N-(2-hydroxyethoxyethyl) propionamide as a waxy solid (0.48 g, 1.25 mmol) (yield 70%).

$[\alpha]_D$=+6 (c=1; $CH_3OH$). $^1$H-NMR ($CDCl_3$): δ 7.78 (d, 2H, J=7 Hz); 6.95 (d, 2H, J=7 Hz); 5.92 (bs, 1H, CONH); 3.68 (m, 2H); 3.55-3.44 (m, 7H); 1.52 (d, 3H, J=7 Hz).

Example 10

R(-)-2-[(4'-trifluoromethanesulfonyloxy)phenyl]-N-[2-(4'-trifluoromethyl)thiazolyl]propionamide A solution of R(-)-2-(4'-trifluoromethanesulfonyloxyphenyl)propionic acid (1.012 g, 3.39 mmol) in thionyl chloride (2 mL) is refluxed under stirring for 2 h. After cooling at room temperature and evaporation under reduced pressure, the crude oily residue is dissolved in $CH_2Cl_2$ (2 mL) and added dropwise to a solution of 2-amino-4-trifluoromethyl thiazole (1.14 g, 6.78 mmol) in $CH_2Cl_2$ (4 mL). 2-amino-4-trifluoromethyl thiazole has been prepared as described in Moazzam M. et al., Indian J. Chem., 27B(11), pages 1051-1053 (1988). The resulting mixture is left stirring at room temperature overnight. The solution is washed with a saturated solution of $NaHCO_3$ (2×5 mL), water (3×10 mL), dried on $Na_2SO_4$ and evaporated under reduced pressure to give a crude oily residue. After treatment of the crude with isopropyl ether overnight at room temperature and filtration of the formed precipitate, pure R(-)-2-[(4'-trifluoromethanesulfonyloxy)phenyl]-N-[2-(4'-trifluoromethyl)thiazolyl]propionamide is isolated as slightly brown solid (0.94 g, 2.10 mmol) (yield 62%).

m.p. 138°-141° C. $[\alpha]_D$=-50 (c=0.5; $CH_3OH$). $^1$H-NMR ($CDCl_3$): δ 10.68 (bs, 1H, CONH); 7.45 (d, 2H, J=7 Hz); 7.28 (d, 2H, J=7 Hz); 7.06 (s, 1H); 3.88 (q, 1H, J=7 Hz); 1.67 (d, 3H, J=7 Hz).

Example 11

R(-)-2-[(4'-trifluoromethanesulfonyloxy)phenyl]-N-methyl-N-hydroxy propionamide

A solution of N,N-dimethylformamide (0.42 mL, 5.42 mmol) in $CH_2Cl_2$ (4 mL) is cooled at T=-20° C. and a solution of oxalyl chloride (0.16 ml; 1.83 mmol) in $CH_2Cl_2$ (5 mL) is added dropwise. At the end of the addings, the T is raised at T=0° C. and, after stirring 30', R(-)-2-(4'-trifluoromethanesulfonyloxyphenyl)propionic acid (0.5 g, 1.67 mmol) and 4-methylmorpholine (0.185 mL, 1.67 mmol) are added. After stirring at T=0° C. for 30' N-methylhydroxylamine hydrochloride (0.27 g, 3.3 mmol) and 4-methylmorpholine (0.73 mL, 6.6 mmol) are added. The temperature is left to raise to room temperature and left stirring overnight. The formed precipitate is filtered off and the mother liquors are evaporated under reduced pressure. The crude oily residue is dissolved in $CH_2Cl_2$ (5 mL) and washed with a 1N HCl (2×5 mL), water (2×10 mL), a saturated solution of $NaHCO_3$ (2×10 mL), dried on $Na_2SO_4$ and evaporated under reduced pressure to give a crude oily residue. Purification of the crude by flash chromatography ($CH_2Cl_2/CH_3OH$ 99:1) affords pure R(-)-2-[(4'-trifluoromethanesulfonyloxy)phenyl]-N-methyl-N-hydroxy propionamide as slightly yellow oil (0.355 g, 1.08 mmol) (yield 65%).

$[\alpha]_D$=-23 (c=1.5; $CH_3OH$). $^1$H-NMR (DMSO-$d_6$): δ 10.05 (bs, 1H, OH); 7.48 (s, 4H); 4.40 (q, 1H, J=7 Hz); 3.10 (s, 3H); 1.40 (d, 3H, J=7 Hz).

Table III reports chemical name and structure formula for the compounds of Examples 1-11.

TABLE III

| Example | Chemical name | Structure Formula |
|---|---|---|
| 1 | R(-)-2-[(4'-trifluoromethanesulfonyloxy)phenyl]-N-methanesulfonyl propionamide | 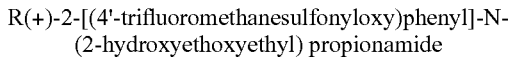 |
| 1a | R(-)-2-[(4'-trifluoromethanesulfonyloxy)phenyl]-N-methanesulfonyl propionamide sodium salt | 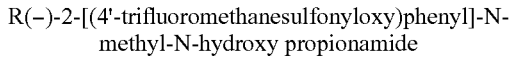 |
| 2 | R(-)-2-[(4'-trifluoromethanesulfonyloxy)phenyl] propionamide | 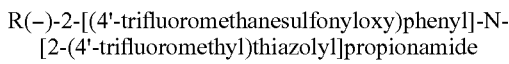 |

TABLE III-continued

| Example | Chemical name |
|---|---|
| 3 | R(−)-2-[(4'-trifluoromethanesulfonyloxy)phenyl]-N-methyl propionamide |
| 4 | R(−)-2-[(4'-trifluoromethanesulfonyloxy)phenyl]-N-isopropoxy propionamide |
| 5 | R(−)-2-[(4'-trifluoromethanesulfonyloxy)phenyl]-N-cyclopentyl propionamide |
| 6 | R(−)-2-[(4'-trifluoromethanesulfonyloxy)phenyl]-N-[3-(N'-piperidinyl)propyl] propionamide |
| 6a | R(−)-2-[(4'-trifluoromethanesulfonyloxy)phenyl]-N-[3-(N'-piperidinyl)propyl] propionamide hydrochloride |
| 7 | R(−)-2-[(4'-trifluoromethanesulfonyloxy)phenyl]-N-[2-(N'-pirrolidinyl)ethyl] propionamide |
| 7a | R(−)-2-[(4'-trifluoromethanesulfonyloxy)phenyl]-N-[2-(N'-pirrolidinyl)ethyl] propionamide hydrochloride |
| 8 | R(−)-2-[(4'-trifluoromethanesulfonyloxy)phenyl]-N-[3-(N'-pirrolidinyl)propyl] propionamide |
| 8a | R(−)-2-[(4'-trifluoromethanesulfonyloxy)phenyl]-N-[3-(N'-pirrolidinyl)propyl] propionamide hydrochloride |

TABLE III-continued

| Example | Chemical name | Structure Formula |
|---|---|---|
| 9 | R(+)-2-[(4'-trifluoromethanesulfonyloxy)phenyl]-N-(2-hydroxyethoxyethyl) propionamide | |
| 10 | R(-)-2-[(4'-trifluoromethanesulfonyloxy)phenyl]-N-[2-(4'-trifluoromethyl)thiazolyl] propionamide | |
| 11 | R(-)-2-[(4'-trifluoromethanesulfonyloxy)phenyl]-N-methyl-N-hydroxy propionamide | |

The invention claimed is:

1. A method for treating psoriasis, ulcerative colitis, melanoma, angiogenesis, chronic obstructive pulmonary disease (COPD), bullous pemphigo, rheumatoid arthritis, idiopathic fibrosis, glomerulonephritis and in the prevention and treatment of ischemia-reperfusion injury, comprising administering to a patient in need thereof a therapeutically effective amount of a 2-(R)-phenylpropionic acid derivative compound of formula (I):

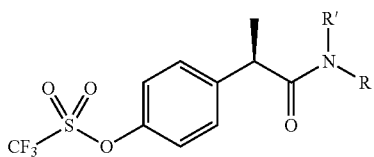

I or a pharmaceutically acceptable salt thereof,
wherein:
R' group is selected from:
  H, OH and
  when R' is H, R is selected from
    H, $C_1$-$C_5$-alkyl, $C_3$-$C_6$-cycloalkyl, $C_2$-$C_5$-alkenyl, $C_1$-$C_5$-alkoxy;
    an heteroaryl group selected from substituted and unsubstituted pyridine, pyrimidine, pyrrole, thiophene, furane, indole, thiazole, oxazole;
    an amino acid residue consisting of straight or branched $C_1$-$C_6$-alkyl, $C_3$-$C_6$-cycloalkyl, $C_2$-$C_6$-alkenyl, $C_1$-$C_6$-phenylalkyl, substituted with one further carboxy (COOH) group;
    a residue of formula —$CH_2$—$CH_2$—Z—($CH_2$—$CH_2$O$)_n$R' wherein R' is H or $C_1$-$C_5$-alkyl, n is an integer from 0 to 2 and Z is oxygen or sulfur;
    a residue of formula —($CH_2)_n$—NRaRb wherein n is an integer from 0 to 5 and each Ra and Rb, which may be the same or different, are $C_1$-$C_6$-alkyl, $C_2$-$C_6$-alkenyl or, alternatively,
    Ra and Rb together with the nitrogen atom to which they are bound, form a heterocycle from 3 to 7 members of formula (II),

(II)

wherein W represents a single bond, O, S, N-Rc, Rc being H, $C_1$-$C_6$-alkyl or $C_1$-$C_6$-alkylphenyl, and n is an integer from 0 to 3,
a residue of formula $SO_2$Rd wherein Rd is $C_1$-$C_6$-alkyl, $C_3$-$C_6$-cycloalkyl, $C_2$-$C_6$-alkenyl, aryl and heteroaryl;
when R' is OH, R is selected from
H, $C_1$-$C_5$-alkyl, $C_3$-$C_6$-cycloalkyl, $C_2$-$C_5$-alkenyl.

2. The method according to claim 1 wherein
when in the compound of formula (I) R' is H, R is selected from
H, $C_1$-$C_5$ alkyl, $C_3$-$C_6$ cycloalkyl, $C_1$-$C_5$ alkoxy, $C_1$-$C_2$-carboxyalkyl;
an heteroaryl group selected from substituted and unsubstituted pyridine, thiazole, oxazole;
a residue of formula —($CH_2)_n$—NRaRb wherein n is the integer 2 or 3, more preferably 3 and the group NRaRb is N,N-dimethylamine, N,N-diethylamine, 1-piperidyl, 1-pyrrolidinyl, 4-morpholyl, 1-pyrrolidyl, 1-piperazinyl, 1-(4-methyl)piperazinyl; a residue of formula $SO_2$Rd wherein Rd is $C_1$-$C_2$-alkyl, $C_3$-$C_6$ cycloalkyl;
when R' is OH, R is
H, $C_1$-$C_5$ alkyl, $C_3$-$C_6$ cycloalkyl.

3. The method according to claim 1 wherein the compound of formula (I) is selected from:
R(-)-2-[(4'-trifluoromethanesulfonyloxy)phenyl]-N-methanesulfonylpropionamide;
R(-)-2-[(4'-trifluoromethanesulfonyloxy)phenyl]-N-methanesulfonylpropionamide sodium salt;
R(-)-2-[(4'-trifluoromethanesulfonyloxy)phenyl]propionamide;
R(-)-2-[(4'-trifluoromethanesulfonyloxy)phenyl]-N-methyl propionamide;
R(-)-2-[(4'-trifluoromethanesulfonyloxy)phenyl]-N-isopropoxy propionamide;

R(−)-2-[(4'-trifluoromethanesulfonyloxy)phenyl]-N-cyclopentyl propionamide;

R(−)-2-[(4'-trifluoromethanesulfonyloxy)phenyl]-N-[3-(N-piperidinyl)propyl]propionamide;

R(−)-2-[(4'-trifluoromethanesulfonyloxy)phenyl]-N-[3-(N'-piperidinyl)propyl]propionamide hydrochloride;

R(−)-2-[(4'-trifluoromethanesulfonyloxy)phenyl]-N-[2-(N'-pyrrolidinyl)ethyl]propionamide;

R(−)-2-[(4'-trifluoromethanesulfonyloxy)phenyl]-N-[2-(N'-pyrrolidinyl)ethyl]propionamide hydrochloride;

R(−)-2-[(4'-trifluoromethanesulfonyloxy)phenyl]-N-[3-(N'-pyrrolidinyl)propyl]propionamide;

R(−)-2-[(4'-trifluoromethanesulfonyloxy)phenyl]-N-[3-(N'-pyrrolidinyl)propyl]propionamide hydrochloride;

R(+)-2-[(4'-trifluoromethanesulfonyloxy)phenyl]-N-(2-hydroxyethoxyethyl) propionamide;

R(−)-2-[(4'-trifluoromethanesulfonyloxy)phenyl]-N-[2-(4'-trifluoromethyl)thiazolyl]propionamide;

R(−)-2-[(4'-trifluoromethanesulfonyloxy)phenyl]-N-methyl-N-hydroxypropionamide.

4. The method according to claim 3 wherein said compound is:

R(−)-2-[(4'-trifluoromethanesulfonyloxy)phenyl]-N-methanesulfonyl propionamide and its sodium salt.

* * * * *